United States Patent
Peterson

(10) Patent No.: US 7,086,402 B2
(45) Date of Patent: Aug. 8, 2006

(54) TRACHEAL TUBE/TRACHEAL CATHETER ADAPTOR CAP

(75) Inventor: Leslie William Peterson, 1321 Ridgetrail Dr., Castle Rock, CO (US) 80104

(73) Assignees: Transtracheal Systems, Inc., Englewood, CO (US); Leslie William Peterson, Castle Rock, CO (US); Peter L. Durante, Aurora, CO (US)

( * ) Notice: Subject to any disclaimer, the term of this patent is extended or adjusted under 35 U.S.C. 154(b) by 0 days.

(21) Appl. No.: 11/243,776

(22) Filed: Oct. 4, 2005

(65) Prior Publication Data

US 2006/0070627 A1     Apr. 6, 2006

Related U.S. Application Data

(60) Provisional application No. 60/616,488, filed on Oct. 5, 2004.

(51) Int. Cl.
   *A61M 16/00*      (2006.01)
   *A62B 9/02*       (2006.01)

(52) U.S. Cl. .................... 128/207.14; 128/207.15; 128/207.16; 128/200.26; 604/93.01

(58) Field of Classification Search .......... 128/207.14, 128/207.15, 207.16, 200.26; 604/93.01
   See application file for complete search history.

(56) References Cited

U.S. PATENT DOCUMENTS

| | | | | | |
|---|---|---|---|---|---|
| 4,009,720 | A | * | 3/1977 | Crandall | 128/207.15 |
| 4,033,353 | A | * | 7/1977 | La Rosa | 128/207.15 |
| 4,315,505 | A | * | 2/1982 | Crandall et al. | 128/200.26 |
| 5,054,482 | A | * | 10/1991 | Bales | 128/207.14 |
| 5,259,376 | A | * | 11/1993 | Bales | 128/207.17 |
| 5,361,754 | A | * | 11/1994 | Stuart | 128/207.17 |
| 5,390,669 | A | * | 2/1995 | Stuart et al. | 128/207.14 |
| 5,419,314 | A | * | 5/1995 | Christopher | 128/200.26 |
| 5,515,844 | A | * | 5/1996 | Christopher | 128/200.26 |
| 5,778,877 | A | * | 7/1998 | Stuart | 128/207.17 |
| 5,819,734 | A | * | 10/1998 | Deily et al. | 128/207.17 |
| 6,105,577 | A | * | 8/2000 | Varner | 128/207.17 |
| 6,135,111 | A | * | 10/2000 | Mongeon | 128/207.15 |
| 6,284,179 | B1 | * | 9/2001 | Deily et al. | 264/254 |
| 6,698,424 | B1 | * | 3/2004 | Madsen et al. | 128/202.27 |

* cited by examiner

*Primary Examiner*—Henry Bennett
*Assistant Examiner*—Nihir Patel
(74) *Attorney, Agent, or Firm*—Sheridan Ross P.C.

(57) ABSTRACT

A device for adapting a transtracheal catheter to a tracheostomy tube includes a plurality of projections for engaging a security flange of the transtracheal catheter. The device provides for proper orientation of a beveled end of the catheter tube when the security flange is oriented as directed with it longest flat side up. A method of adapting a transtracheal catheter to a patient's tracheostomy tube is also provided for providing the delivery of heated and/or humidified gas to tracheotomized patients and/or for weaning a ventilator-dependent patient from the ventilator.

24 Claims, 5 Drawing Sheets

US 7,086,402 B2

TRACHEAL TUBE/TRACHEAL CATHETER ADAPTOR CAP

CROSS REFERENCE TO RELATED APPLICATIONS

The present application claims the benefit of U.S. Provisional Patent Application No. 60/616,488 filed on Oct. 5, 2004 and entitled "Tracheal Oxygen Adaptor Cap," which is incorporated herein by reference in its entirety.

FIELD OF THE INVENTION

The present invention relates to a medical device that operates in association with a tracheostomy tube, and more particularly, a device for adapting a catheter to a tracheostomy tube.

BACKGROUND OF THE INVENTION

U.S. Pat. No. 5,515,844 entitled "Method and Apparatus for Weaning Ventilator-Dependent Patients," incorporated herein by reference in its entirety, discloses several adapter devices used in connection with methods for weaning ventilator-dependent patients who access oxygen from the ventilator through a tracheostomy tube. The methods include deflating the cuff on the patient's tracheostomy tube and supplying a continuous flow of oxygen or an air mixture through a transtracheal catheter fitted into the patient's tracheostomy tube and into the patient's lungs. In addition to weaning a ventilator-dependent patient from a ventilator, it has also been found that tracheotomized patients may benefit from receiving heated and/or humidified gas, such as oxygen, air, air/oxygen blend, etc., from a transtracheal catheter.

The adapter devices of the '844 patent include a tapered plug or cap to block the opening of the tracheostomy tube. However, the adapter devices of the '844 patent are generally not configured to directly attach to the security flange of the transtracheal catheter. More particularly, the adapter devices of the '844 patent are not configured to directly interconnect with the security flange of the transtracheal catheter sold under the trademark SCOOP® and manufactured by Transtracheal Systems, Inc. of Englewood, Colo., and described in U.S. Pat. Nos. 5,090,408 and 5,181,509, incorporated herein by reference in their entirety. As shown in FIG. 1, the transtracheal catheter 10 sold under the trademark SCOOP® includes a tube 14 having a connector 18 at is proximal end for attachment to an oxygen/air supply. In addition, the transtracheal catheter 10 has a distal end having a beveled end 22. The transtracheal catheter 10 is made of a bio-polymer of 70–90 Shore A durometer hardness that resists kinking and crushing. The transtracheal catheter 10 further includes a security flange 26 having two holes 30 for accepting a small chain (not shown) for maintaining the position of the transtracheal catheter 10 around the patient's neck.

Referring now to FIG. 2, a tracheostomy tube assembly 34 of the prior art is shown. The assembly 34 includes an outer cannula 38 and a sealing balloon 42 located adjacent the distal end 46 of the outer cannula 38. Positioned adjacent the proximal end 50 of the outer cannula 38 is a swivel neck flange 54 that is used to secure the assembly 34 to the neck of the patient. A flexible inflation tube 58 extends from the proximal end 50 of the outer cannula 38 to receive air to inflate the balloon 42 for sealing the outer cannula 38 within the trachea of the patient.

Referring now to FIG. 3, the outer cannula 38 includes a coupling mechanism or connector 62 for removably attaching an inner cannula 66 to the outer cannula 38. Comparing FIG. 3 to FIG. 2, the inner cannula 66 is partially removed from within the outer cannula 38. The inner cannula 66 includes a tube fitting 70 at its proximate end. The inner cannula 66 is designed to be completely removed from within the outer cannula 38 in order to allow the inner cannula 66 to periodically be cleaned and thereby provide a clean and clear passage for the flow of air to the patient.

While the adapter devices of the '844 patent may be utilized along a position of the tube 14 of the transtracheal catheter 10, the adapter devices of the '844 patent do not secure the transtracheal catheter in place. Rather, the transtracheal catheter is typically independently secured by a chain around the patient's neck. More specifically, the adapter devices of the '844 patent do not engage the security flange 26 of a transtracheal catheter 10. Therefore, it would be advantageous to provide a tracheostomy tube adapter for direct use with the security flange 26 of the transtracheal catheter 10 sold under the trademark SCOOP®. In addition, it would be advantageous to provide a tracheostomy tube adapter that properly orients the beveled end 22 of the transtracheal catheter 10 within the tracheostomy tube assembly 34.

SUMMARY OF THE INVENTION

The present invention solves the above-mentioned deficiencies by providing an adapter device for adapting a transtracheal catheter to a tracheostomy tube. Transtracheal catheters typically include a tube and a security flange connected to the tube. In accordance with embodiments of the present invention, an adapter device is provided comprising a perimeter wall, wherein the perimeter wall provides a means for engaging the tracheostomy tube, and in at least one embodiment, forms a friction fit with the tracheostomy tube. The perimeter wall may comprise a shape allowing the adapter to either plug into or fit over a portion of the tracheostomy tube. The perimeter wall also includes an aperture or a means for receiving the tube of the transtracheal catheter. The adapter device further includes at least one projection connected to the perimeter wall, wherein the projection is for engaging the security flange of the transtracheal catheter. In accordance with at least some of the embodiments of the present invention, the adapter device may further comprise at least one flange portion connected to the perimeter wall, wherein at least a portion of the flange portion has a shape substantially matching a portion of a shape of the security flange. This allows the security flange of the transtracheal catheter and the adapter device to be quickly aligned in a proper orientation relative to each other. In addition, the adapter device may further comprise at least a second projection connected to the perimeter wall, wherein the second projection is for engaging a different portion of the security flange of the transtracheal catheter than the first projection. In accordance with at least some of the embodiments of the present invention, the two projections are located on opposing sides of the perimeter wall. In addition, in accordance with at least some of the embodiments of the present invention, the projections are positioned to prevent rotation and/or longitudinal movement of the transtracheal catheter relative to the tracheostomy tube. In accordance with at least some of the embodiments of the present invention, the projection comprises a center that is aligned within a width of the perimeter wall. In accordance with at least some of the embodiments of the present invention, the projection includes at least a first portion having a first diameter and a second portion having a second diameter, wherein the first diameter is greater than the second diameter. In addition, in accordance with at least some of the embodiments of the present invention, the projection may include at least a third portion having a third diameter, wherein the first portion is located between the second and third portions, and wherein the first diameter is greater than the third diameter.

In accordance with at least some of the embodiments of the present invention, a method of adapting a transtracheal catheter to a patient's tracheostomy tube is also provided for providing the delivery of heated and/or humidified gas (oxygen, air, air/oxygen blend, etc.) to tracheotomized patients and/or for weaning a ventilator-dependent patient from the ventilator. The method includes (1) ventilating the patient with a tracheostomy tube having a proximal opening connected to a ventilator, a distal opening inserted through an incision into the patient's trachea, and an inflatable balloon about the tracheostomy tube adjacent the distal opening for sealing the region between the tracheostomy tube and the patient's trachea; (2) disconnecting the ventilator from the proximal opening of the tracheostomy tube; (3) deflating the balloon so that the patient can breathe spontaneously through the patient's upper airway; (4) removably inserting a transtracheal catheter through the adapter and into the tracheostomy tube; (5) connecting an adapter to the proximal opening of the tracheostomy tube; (6) engaging at least one projection of the adapter with a security flange of the transtracheal catheter; and (7) supplying a prescribed flow of an oxygen/air/gas mixture through the transtracheal catheter and into the lungs of the patient. Prior to engaging the projections, the method may further comprise aligning a flange portion of the adapter with the security flange to properly orient the adapter. In addition, in accordance with embodiments of the present invention, the step of connecting an adapter to the proximal opening of the tracheostomy tube may be performed prior to the step of removably inserting a transtracheal catheter through the tracheostomy tube, and the method may further comprise removably inserting the transtracheal catheter into the adapter.

Various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

Several drawings have been developed to assist with understanding the invention. Following is a brief description of the drawings that illustrate the invention and its various embodiments.

DETAILED DESCRIPTION OF THE INVENTION

Figure 1:
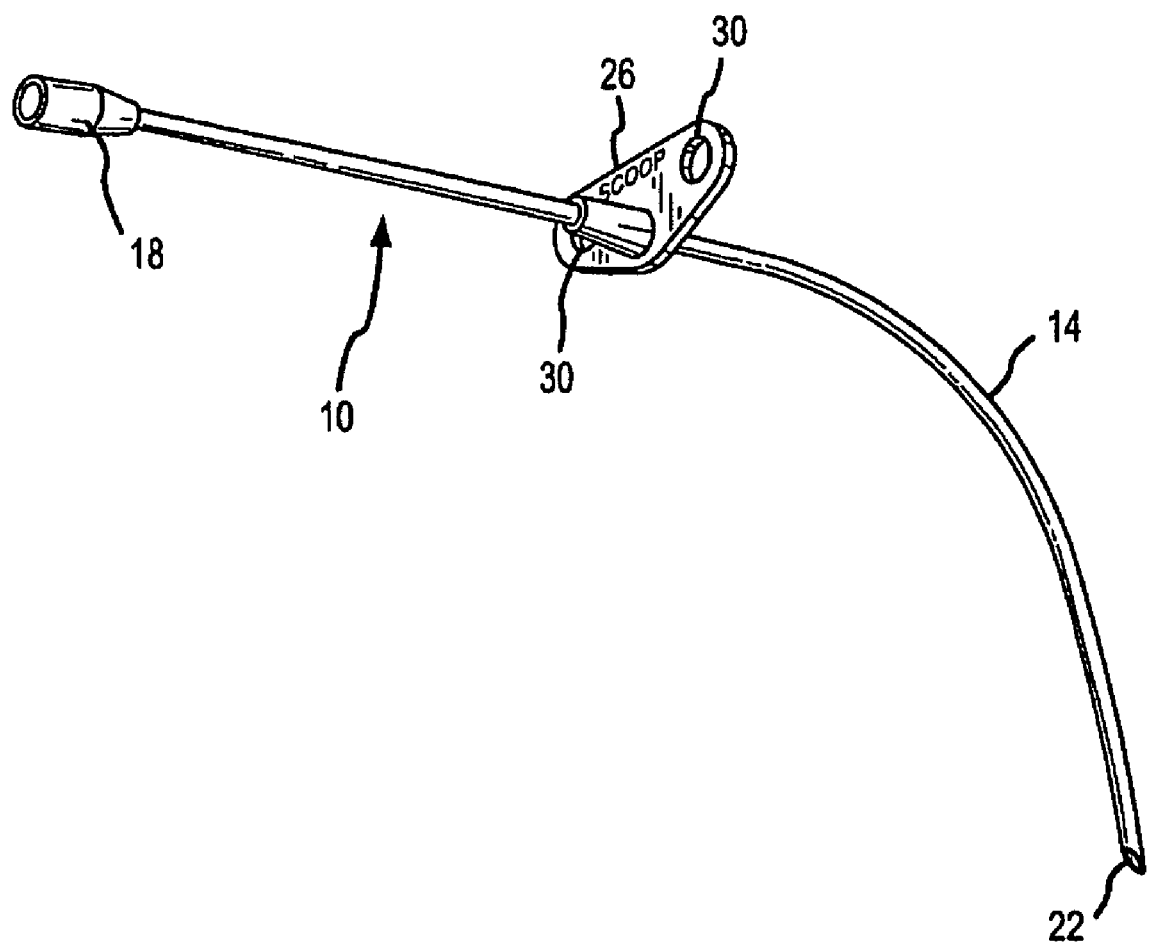
FIG. 1 is a perspective view of a transtracheal catheter sold under the trademark SCOOP®.
Figure 2:
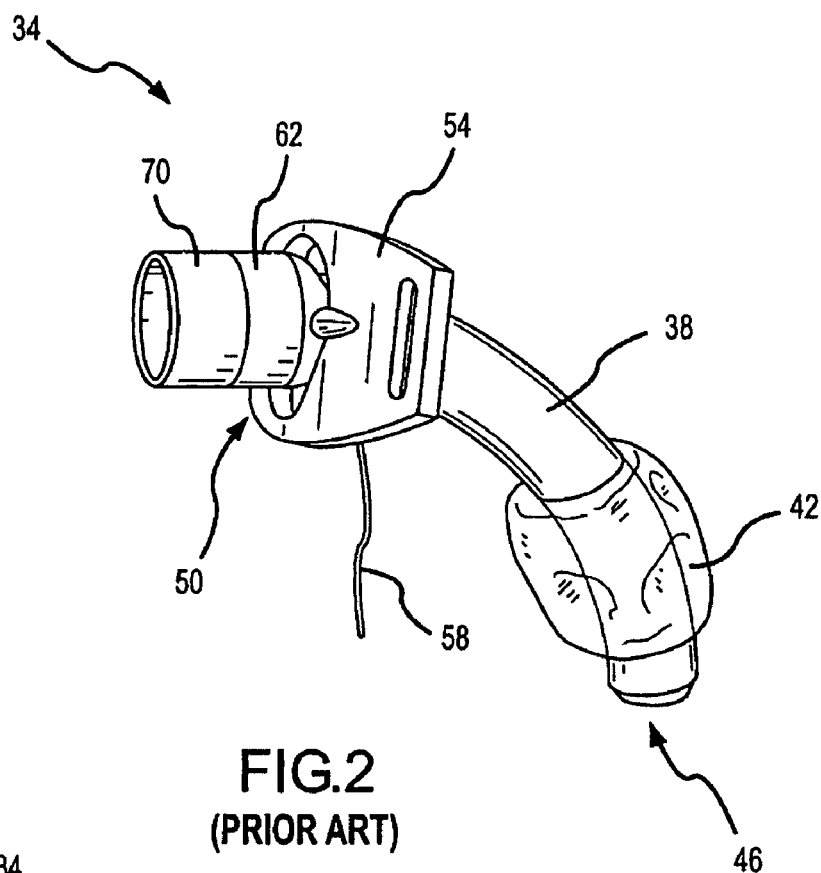
FIG. 2 is a perspective view of a tracheostomy tube known in the prior art.
Figure 3:
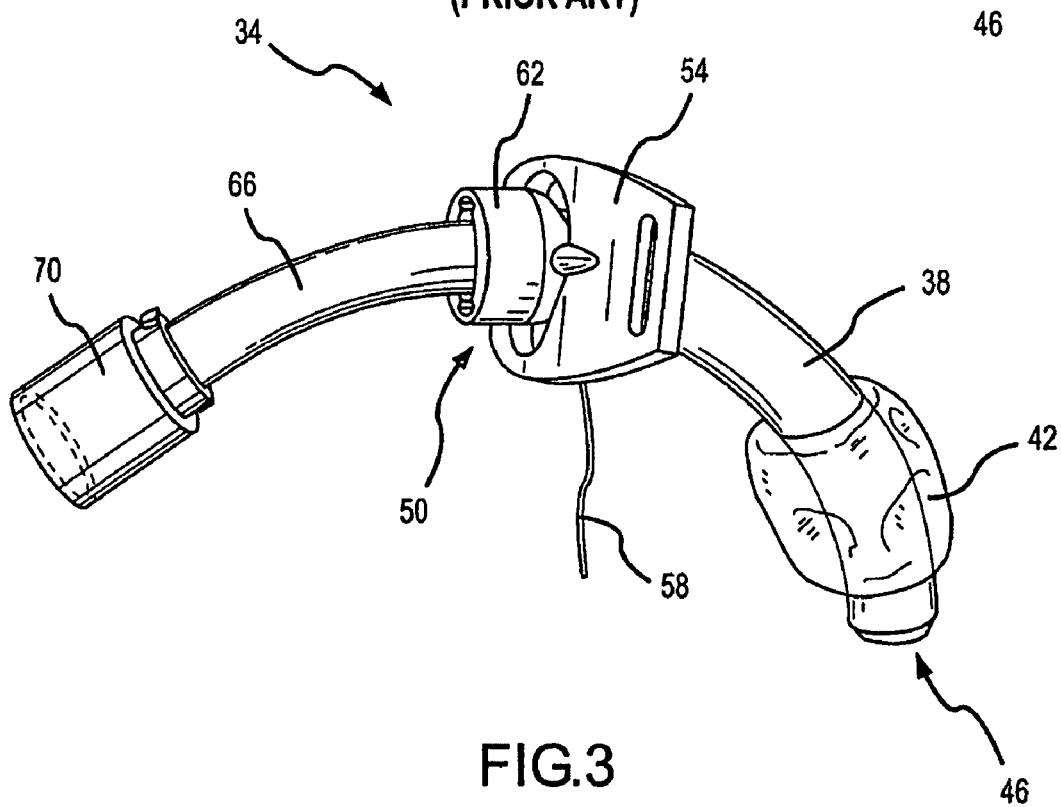
FIG. 3 is a perspective view of the tracheostomy tube shown in FIG. 2, and further illustrating the inner cannula of the tracheostomy tube.
Figure 4:
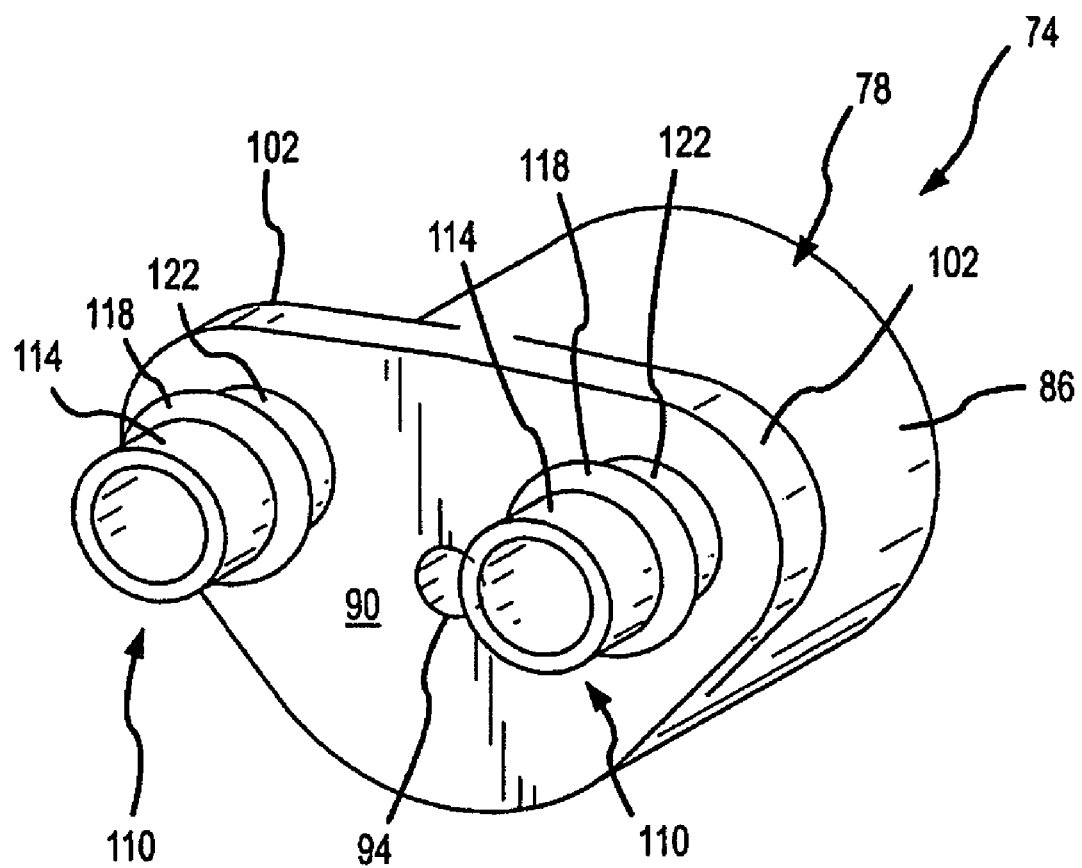
FIG. 4 is a perspective view of an embodiment of the present invention.

Referring now to FIGS. 4–10, in accordance with embodiments of the present invention, a device for adapting a transtracheal catheter to a tracheostomy tube is shown. The present invention comprises an adapter cap 74 for attachment to the connector 62 at the proximal end 50 of the tracheostomy tube assembly 34. Accordingly, the cap 74 is a device to allow the transtracheal catheter 10 of FIG. 1 to be inserted directly into the tracheostomy tube assembly 34 of FIGS. 2 and 3 after removal of the inner cannula 66 from the outer cannula 38.

The adapter cap 74 includes a cylindrical wall 78 having an inner surface 82 and an outer surface 86. In addition, the cap 74 includes an end wall 90, wherein the end wall 90 includes an aperture 94 for receiving the tube 14 of the transtracheal catheter 10. The end wall 90 and the cylindrical wall 78 act as a perimeter wall that define a chamber 98 that acts as a receptacle for receiving the connector 62 at the proximal end 50 of the tracheostomy tube assembly 34. When the cap 74 is slipped over the connector 62 of the tracheostomy tube assembly 34, the inner surface 82 forms a friction fit with the outer surface of the connector 62. As one skilled in the art will appreciate, although not shown, the cap 74 may also comprise a plug that fits into the interior of the connector 62 or the proximal end 50 of the tracheostomy tube, thereby creating a friction fit with the inside of the connector or tracheostomy tube instead of the outside of the connector.

Figure 6:
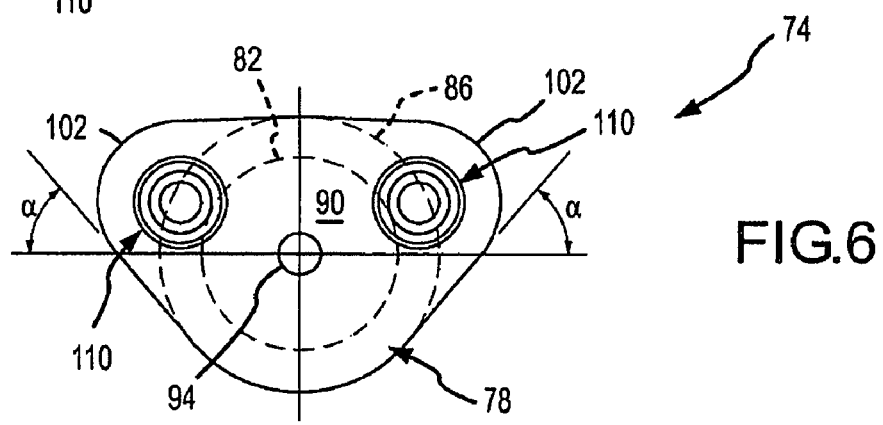
FIG. 6 is a front elevation view of the device shown in FIG. 4.

Contiguous with the end wall 90, the adapter cap 74 preferably includes first and second flange portions 102. The flange portions 102 extend beyond the outer surface 86 of the cylindrical wall 78 and provide a portion of the cap 74 for grasping during the process of fitting the cap 74 to the tracheostomy tube assembly 34. In addition, the flange portions 102 provide an outline or template that substantially matches at least a portion of the shape of the security flange 26 of the transtracheal catheter 10, thereby aiding the person placing the transtracheal catheter 10 into the tracheostomy tube assembly 34 because the shapes of the surfaces can be matched and aligned. This reduces the time for the conversion process, thereby improving patient health because of less time without oxygen. In addition, the speed of the conversion process also aids in decreasing possible mental anxiety and emotional stress to the patient, where such stress can be associated with a breathing problem or a fear of insufficient oxygen during the conversion process. Referring to FIG. 6, from a horizontal, the sides of the flange portions 102 are offset from a horizontal at a side angle α, where the side angle α substantially matches the side angle of the flange 26 of the transtracheal catheter 10. In accordance with the preferred embodiments of the present invention, the side angle α is about 50 degrees.

Figure 5:
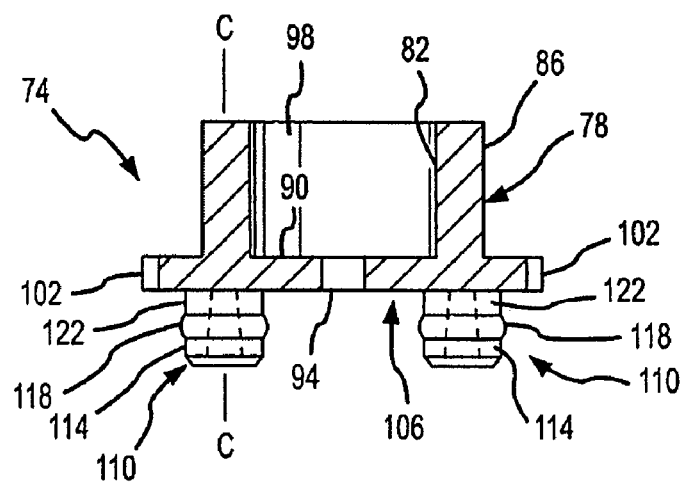
FIG. 5 is a cross-section view of the device shown in FIG. 4.
Figure 7:
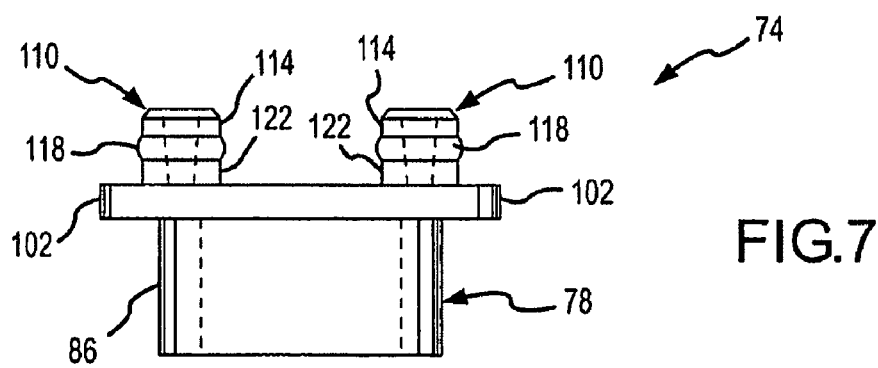
FIG. 7 is a top elevation view of the device shown in FIG. 4.
Figure 8:
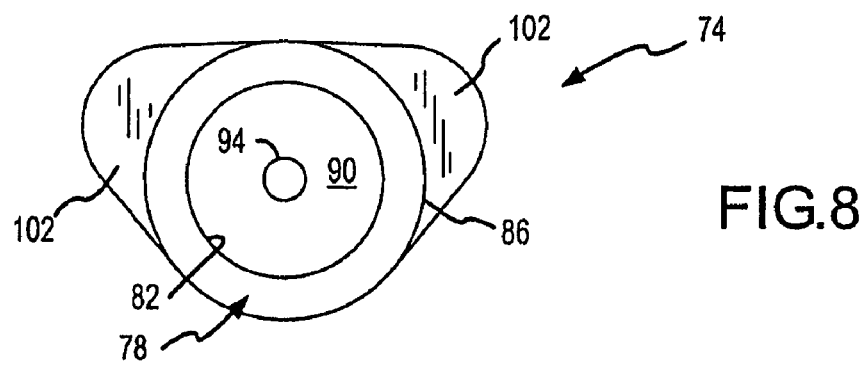
FIG. 8 is a rear elevation view of the device shown in FIG. 4.

As best seen in FIGS. 5 and 7, extending from the front surface 106 of the cap 74 is at least one projection 110, and more preferably, two projections 110. The projections 110 are sized to engage the holes 30 of the security flange 26 of the transtracheal catheter 10. In accordance with at least some embodiments of the present invention, the two projections 110 are located on substantially opposite sides of the cylindrical wall 78 that is located on the opposing side of the end wall 90 of the security flange 26. The projections 110 are preferably positioned to prevent rotation and/or longitudinal movement of the transtracheal catheter relative to the tracheostomy tube. Thus, the projections 110 serve not only as a means to secure the security flange 26 to the adapter cap 74, but the projections 110 also serve to prevent movement of the transtracheal catheter relative to the tracheostomy tube.

Still referring to FIGS. 5 and 7, in accordance with at least some embodiments of the present invention, the projections 110 include three sections along their longitudinal length, including an outer portion 114, a middle portion 118, and an inner portion 122, wherein the middle portion 118 is located between the outer portion 114 and the inner portion 122, and wherein the middle portion 118 has a greater outside diameter than the outer portion 114 and the inner portions 122. The greater outside diameter of the middle portion 118 helps secure the security flange 26 of the transtracheal catheter 10 to the cap 74 because the projections 110 are advanced through the holes 30 of the security flange 26 until the outer surface or wall of the security flange 26 passes by the middle portion 118 of the projections 110. More particularly, the pliable material forming the security flange 26 allows the material to expand around the greater outside diameter of the middle portion 118 of the projections 110, wherein the middle portion 118 of the projections 110 retains the security flange 26 to the cap 74. In accordance with at least some of the embodiments of the present invention, the center "c" of each projection 110 is aligned to intersect the cylindrical wall 78, thereby improving the structural integrity of the cap 74.

The cap 74 is preferably formed of a medical grade polyurethane of between about 70 to 90 Shore A durometer hardness, and more preferably, is formed of a medical grade polyurethane of about 80 Shore A durometer hardness. However, as those skilled in the art will appreciate, the cap may be formed of other materials, including composites and combinations of materials used to form different portions of the cap 74.

Figure 9:
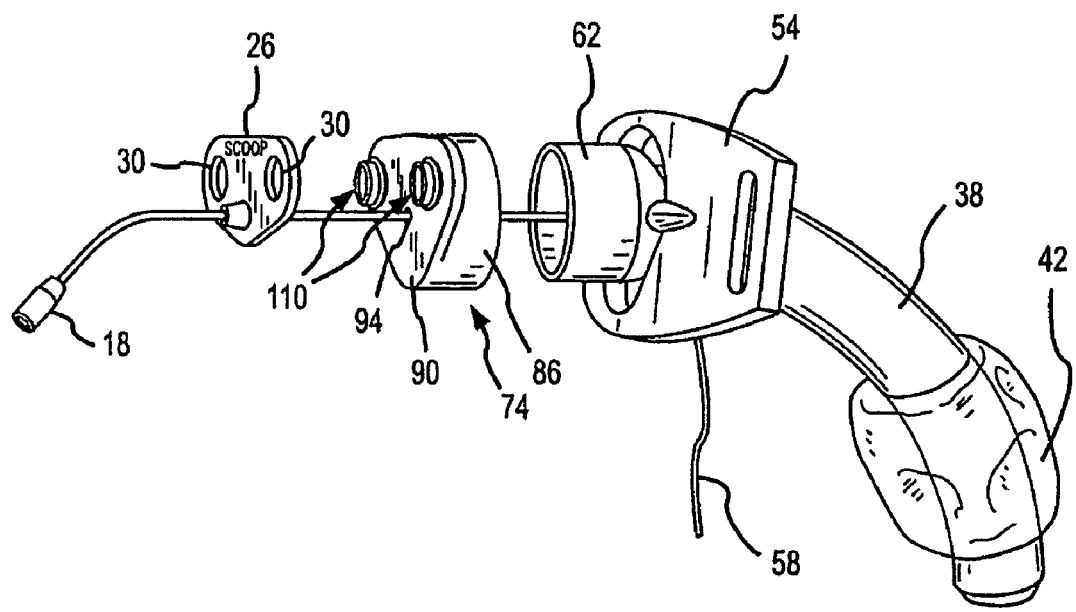
FIG. 9 is an exploded perspective view of an assembly including a transtracheal catheter, tracheostomy tube, and an adapter device in accordance with embodiments of the present invention, the adapter for interconnecting the transtracheal catheter and the tracheostomy tube.

Referring now to FIG. 9, an exploded view of a transtracheal catheter sold under the trademark SCOOP®, a tracheostomy tube, and a cap 74 in accordance with embodiments of the present invention are shown. As can be seen from FIG. 9, the inner surface 82 of the cylindrical wall 78 is aligned to slide over the outer surface of the connector 62 of the tracheostomy tube. More particularly, the inner cannula 66 is preferably removed from the outer cannula 38, and then the inner surface 82 of the cylindrical wall 78 is aligned to slide over the connector 62. In addition, as described above, the flange portions 102 provide an outline or template that substantially matches a portion of the shape of the security flange 26 of the transtracheal catheter 10, thereby aiding the person placing the transtracheal catheter 10 into the tracheostomy tube assembly 34 by providing a visual aid for aligning the flange 26 with the adapter cap 74. During assembly, the tube 14 of the transtracheal catheter is placed though aperture 94 of the cap 74.

Figure 10:
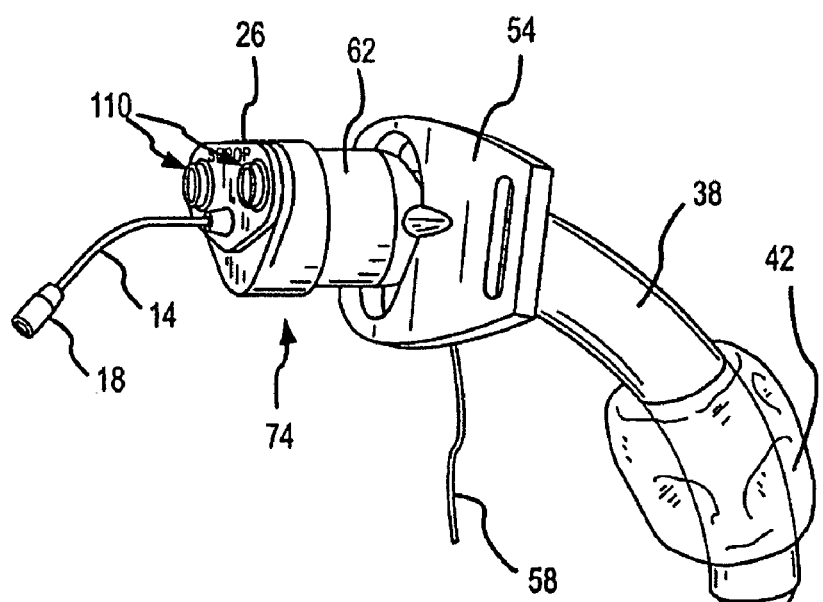
FIG. 10 is a perspective view of the fully assembled transtracheal catheter, tracheostomy tube, and adapter shown in FIG. 9.

Referring now to FIG. 10, upon assembly, at least a portion of the projections 110 are placed through the holes 30 of the security flange 26 until the outer surface or wall of the security flange 26 passes by the middle portion 118 of the projections 1 10. With the transtracheal catheter 10 fitted to the cap 74, and the cap 74 fitted to the tracheostomy tube, the assembly is complete. The adapter cap 74 permits the tracheostomy tube 34 to readily be transformed for use with a transtracheal catheter.

In accordance with embodiments of the present invention, a method of adapting a transtracheal catheter to a patient's tracheostomy tube is provided for the delivery of heated and/or humidified gas (oxygen, air, air/oxygen blend, etc.) to tracheotomized patients and/or for weaning a ventilator-dependent patient from the ventilator. The method employs a transtracheal tube or catheter that is inserted through the patient's tracheostomy tube to augment the flow of oxygen, air, or gas mixtures to the lungs as the patient breathes spontaneously. The gas delivery and/or weaning process involves disconnecting the ventilator from the tracheostomy tube; deflating the tracheostomy tube balloon so that the patient can breathe spontaneously through the upper airway; removably inserting a transtracheal catheter or tube through an adapter and into the tracheostomy tube; connecting an adapter to the proximal opening of the tracheostomy tube; engaging at least one projection of the adapter with a security flange of the transtracheal catheter; and supplying a prescribed flow of an oxygen/air/gas mixture through the transtracheal catheter and into the lungs of the patient. The method may also include the step of aligning a flange portion of the adapter with the security flange to properly orient the adapter. In addition, in accordance with at least some embodiments of the present invention, the inner cannula, if present, is removed from the outer cannula of the tracheostomy tube assembly prior to insertion of the transtracheal catheter into the tracheostomy tube.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance or achieving ease and\or reducing cost of implementation.

The foregoing discussion of the invention has been presented for purposes of illustration and description. The foregoing is not intended to limit the invention to the form or forms disclosed herein. In the foregoing Detailed Description of the Invention, for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description Of The Invention, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those skilled in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An adapter device for adapting a transtracheal catheter to a tracheostomy tube, the transtracheal catheter including a tube and a security flange connected to the tube, the adapter device comprising:
    a perimeter wall, wherein said perimeter wall engages the tracheostomy tube, the perimeter wall including an aperture for receiving the tube of the transtracheal catheter; and
    at least one projection connected to the perimeter wall, said projection for engaging the security flange of the transtracheal catheter.

2. The adapter device as claimed in claim 1, further comprising at least one flange portion connected to the perimeter wall, wherein at least a portion of the flange portion has a shape substantially matching a portion of a shape of the security flange.

3. The adapter device as claimed in claim 1, further comprising at least a second projection connected to the perimeter wall, said second projection for engaging the security flange of the transtracheal catheter.

4. The adapter device as claimed in claim 3, wherein said first projection is located on a first side of the perimeter wall, and said second projection is located on an opposing side of the perimeter wall.

5. The adapter device as claimed in claim 3, wherein said first and second projections are positioned to prevent at least one of (a) a rotation of the transtracheal catheter relative to the tracheostomy tube, and (b) a longitudinal movement of the transtracheal catheter relative to the tracheostomy tube.

6. The adapter device as claimed in claim 1, wherein said projection comprises a center that is aligned with a cylindrical wall portion of said perimeter wall.

7. The adapter device as claimed in claim 1, wherein said perimeter wall comprises a receptacle for receiving a portion of the tracheostomy tube.

8. The adapter device as claimed in claim 1, wherein the tracheostomy tube has an interior surface, and said perimeter wall comprises a plug that engages the interior surface of the tracheostomy tube.

9. The adapter device as claimed in claim 1, wherein the tracheostomy tube has an exterior surface, and said perimeter wall includes an inner surface that engages the exterior surface of the tracheostomy tube.

10. The adapter device as claimed in claim 1, wherein said projection includes at least a first portion having a first diameter and a second portion having a second diameter, wherein said first diameter is greater than said second diameter.

11. The adapter device as claimed in claim 10, wherein said projection includes at least a third portion having a third diameter, wherein said first portion is located between said second and third portions, and wherein said first diameter is greater than said third diameter.

12. An adapter device for adapting a transtracheal catheter to a tracheostomy tube, the transtracheal catheter including a tube and a security flange connected to the tube, the adapter device comprising:
    means for engaging the tracheostomy tube, said means for engaging including a means for receiving the tube of the transtracheal catheter; and
    means for removably attaching the means for engaging to the security flange.

13. The adapter device as claimed in claim 12, wherein said means for removably attaching includes a means for retaining an edge of the security flange.

14. The adapter device as claimed in claim 12, further comprising a means for orienting operatively associated with the means for engaging, wherein said means for orienting provides visual guidance for aligning said means for engaging with the security flange.

15. The adapter device as claimed in claim 12, wherein said means for removably attaching further serves as a means for preventing at least one of (a) a rotation of the transtracheal catheter relative to the tracheostomy tube, and (b) a longitudinal movement of the transtracheal catheter relative to the tracheostomy tube.

16. A method for providing delivery of gas to a tracheotomized patient, the patient having an upper airway including a trachea, comprising:
    ventilating the patient with a tracheostomy tube having a proximal opening connected to a ventilator, a distal opening inserted through an incision into the patient's trachea, an inflatable balloon about the tracheostomy tube adjacent the distal opening for sealing the region between the tracheostomy tube and the patient's trachea;
    disconnecting the ventilator from the proximal opening of the tracheostomy tube;
    deflating the balloon so that the patient can breathe spontaneously through the patient's upper airway;
    removably inserting a transtracheal catheter through the tracheostomy tube;
    connecting an adapter to the proximal opening of the tracheostomy tube;
    engaging projections of the adapter with a security flange of the transtracheal catheter; and
    supplying a prescribed flow of gas through the transtracheal catheter and into the lungs of the patient.

17. The method as claimed in claim 16, further comprising aligning a flange portion of the adapter with the security flange to properly orient the adapter.

18. The method as claimed in claim 16, wherein the projections include at least a first portion having a first diameter and a second portion having a second diameter, wherein said first diameter is greater than said second diameter.

19. The method as claimed in claim 18, wherein the projections include at least a third portion having a third diameter, wherein said first portion is located between said second and third portions, and wherein said first diameter is greater than said third diameter.

20. The method as claimed in claim 16, wherein connecting the adapter to the proximal opening of the tracheostomy tube further comprises preventing at least one of (a) a rotation of the transtracheal catheter relative to the tracheostomy tube, and (b) a longitudinal movement of the transtracheal catheter relative to the tracheostomy tube.

21. The method as claimed in claim 16, wherein the step of connecting an adapter to the proximal opening of the tracheostomy tube occurs prior to the step of removably inserting a transtracheal catheter through the tracheostomy tube.

22. The method as claimed in claim 21, further comprising removably inserting the transtracheal catheter into the adapter.

23. The method as claimed in claim 16, wherein the gas is heated and/or humidified.

24. The method of claim 16, wherein the gas comprises at least one of oxygen, air or a mixture containing oxygen and air.

* * * * *